United States Patent [19]

Kato et al.

[11] Patent Number: 4,900,724

[45] Date of Patent: Feb. 13, 1990

[54] TUMOR NECROSIS FACTOR INDUCING SUBSTANCE DERIVED FROM ACID-FAST BACTERIA

[75] Inventors: Yoshiko Kato, Hyogo; Hiroko Usami, Tokyo, both of Japan

[73] Assignees: Sawai Pharmaceutical Co., Ltd; Chugai Seiyaku Kabushiki Kaisha, both of Osaka, Japan

[21] Appl. No.: 931,690

[22] PCT Filed: Mar. 4, 1986

[86] PCT No.: PCT/JP86/00107

§ 371 Date: Nov. 3, 1986

§ 102(e) Date: Nov. 3, 1986

[87] PCT Pub. No.: WO86/05204

PCT Pub. Date: Sep. 12, 1986

[30] Foreign Application Priority Data

Mar. 4, 1985 [JP] Japan .................................. 60-42264

[51] Int. Cl.$^4$ ..................... A61K 35/74; A61K 37/00; C12P 1/00
[52] U.S. Cl. ........................................ 514/62; 424/92; 536/55.2
[58] Field of Search ............................ 514/62; 424/92; 536/55.2

[56] References Cited

U.S. PATENT DOCUMENTS

| | | | |
|---|---|---|---|
| 4,309,418 | 1/1982 | Green | 424/85.2 |
| 4,447,355 | 5/1984 | Sakamoto et al. | 424/85.2 |
| 4,495,282 | 1/1985 | Ohnishi et al. | 435/68 |
| 4,529,594 | 7/1985 | Hayashi et al. | 424/85.1 |
| 4,770,995 | 9/1988 | Rubin et al. | 435/7 |

FOREIGN PATENT DOCUMENTS 725938 3/1955 United Kingdom .
2088399 6/1982 United Kingdom .
2137649 10/1984 United Kingdom .

OTHER PUBLICATIONS

Azuma et al., "Adjuvant and Antitumor Activities of Nocardia Cell-Wall Skeletons", *Chemical Abstracts,* vol. 86, No. 3, 1977, p. 293, Abstract 86:15034p.

M. T. Kelly et al., "Tumor Regression with Q Fever Rickettsiae and a Mycobacterial Glycolipid", *Chemical Abstracts,* vol. 87, No. 22, 1977, p. 57, Abstract 87:177820q.

J. L. Cantrell et al., "Antitumor Activity and Lymphoreticular Stimulation Properties of Fractions Isolated from Corynebacterium Parvum", *Chemical Abstracts,* vol. 91, No. 23, 1979, p. 53, Abstract 91:186679k.

Lederer et al., "Cell Walls of Mycobacteria and Related Organisms; Chemistry and Immunostimulant Properties", *Molecular & Cellular Biochemistry, vol. 7, No. 2, 1975, pp. 87–104.*

S. Haskill et al., "Effect of C. Parvum on Intratumor Immunity to the T1699 Mammary Adenocarcinoma", *The Journal of Immunology,* vol. 125, No. 1, 1980, pp. 454–458.

Primary Examiner—Ronald W. Griffin
Attorney, Agent, or Firm—Browdy and Neimark

[57] ABSTRACT

The present invention provides a novel amphipathic substance having tumor necrosis factor (TNF) inducing activity. This substance is an amphipathic substance obtained by extraction from several kinds of acid-fast bacteria, and has excellent TNF inducing activity. The toxicity of the substance is much lower than that of the conventional amphipathic substances having TNF inducing activity.

16 Claims, No Drawings

TUMOR NECROSIS FACTOR INDUCING SUBSTANCE DERIVED FROM ACID-FAST BACTERIA

TECHNICAL FIELD:

The present invention relates to an amphipathic substance having tumor necrosis factor (TNF) inducing activity which is obtained from acid-fast bacteria by means of extraction. The amphipathic substance according to the present invention is novel and may effectively be employed as a medicine, e.g., an antitumor agent.

BACKGROUND ART:

Lipoteichoic acid (hereinafter referred to as "LTA"), lipopolysaccharide (hereinafter referred to as "LPS") and the like have heretofore been known as amphipathic substances which are extracted from, for example, the whole cell of Gram-positive bacteria and Gram-negative bacteria or a fraction including the cell wall and cytoplasmic membrane of such bacteria (such fraction being referred to as a "cell envelope fraction", hereinafter).

In 1975, Old et al, reported a tumor necrosis factor (TNF) which is a glycoprotein that specifically attacks only tumor cells without damaging normal cells (Proc. Natl. Acad. Sci. U.S.A., 72, 3666). According to this report, it is possible to induce TNF in serum by administering live BCG or the like into the vein of a mouse and administering LPS one to two weeks later. However, the lethal toxicity of LPS is extremely high; for example, if 0.8 $\mu$g/head or more of LPS is administered to mice sensitized with BCG, the greater part of the mice will die within six hours. Accordingly, employment of LPS itself as a medicine such as a cancer controlling agent involves clinical problems.

DISCLOSURE OF THE INVENTION:

The present invention relates to an amphipathic substance having TNF inducing activity which is obtained by extraction from acid-fast bacteria which belong to a range which is different from those to which Gram-positive bacteria and Gram-negative bacteria belong. The amphipathic substance according to the present invention is distinguished from LTA in that the glycerol content in the novel substance is less than the limit of detection and the organic phosphorus content therein is exceedingly lower than that in LTA. Further, the amphipathic substance of the present invention also differs from LPS in that the novel substance contains no hydroxy fatty acid such as 3-hydroxy myristic acid. The chemical composition of the amphipathic substance according to the present invention is as follows (mg/mg; mole/mg for organic phosphorus):

| hexose | 0.25–0.55 |
|---|---|
| pentose | 0.10–0.17 |
| fatty acid | 0.03–0.16 |
| amino acid | 0.07–0.17 |
| amino sugar | <0.03 (generally, 0.001–0.03) |
| organic phosphorus | 0.3–1.7 |
| glycerol | not detected |

In the above chemical composition, the greater part of the hexose consists of mannose, while the greater part of the pentose consists of arabinose. The fatty acid contains palmitic acid, stearic acid and tuberculostearic acid as principal components, and no hydroxy fatty acid is detected. Chief amino acids are glutamic acid, aspartic acid, leucine, threonine, glycine, alanine, serine and valine, and a trace of diaminopimelic acid is detected. The amino sugar consists mainly of glucosamine and contains substantially no muramic acid.

The acid-fast bacteria having the novel amphipathic substance of the present invention are aerobic bacteria which show acid-fast property in cell staining and have in their cell walls a large amount of fatty acids, particularly mycolic acid which is an $\alpha$-branched, $\beta$-hydroxy higher fatty acid. Practical examples of such acid-fast bacteria include species and strains which belong to genera *Mycobacterium, Nocardia, Rhodococcus, Gordona* and *Corynebacterium*. The number of carbon atoms of the mycolic acid which is a constituent component characteristic of the cell walls of these acid-fast bacteria is different for each genus: 60–90 for genus *Mycobacterium*: 30–70 for genera *Nocardia* and *Rhodococcus*: 60–80 for genus *Gordona*: and 30–40 for genus *Corynebacterium*.

Practical examples of the acid-fast strains which may be employed in the present invention include those mentioned below. However, the present invention is not necessarily limited thereby.

*Mycobacterium tuberculosis* H37Rv (ATCC 25618 or 27294)

*Nocardia rubra* Tsukamura collection M-1 (ATCC 27836)

*Rhodococcus terrae* Tsukamura collection 70012 (ATCC 25594)

*Gordona aurantiaca* Tsukamura collection 80005 (ATCC 25938)

Although amphipathic substances according to the present invention may be slightly different from each other in terms of the chemical composition and the chemical structure depending upon the genera to which the employed bacteria belong and upon the species and strains in each genus, all the amphipathic substances have TNF inducing activity.

The amphipathic substance according to the present invention is extracted in an aqueous layer by treating, for example, the whole cell or a cell envelope fraction as a starting material with a phenol/water (1:1, v/v) solution at room temperature. This phenol/water method is a known technique which is represented by the method of Ofek et al. (J. Exp. Med., 141, 990–1003) which is a modification of the method of Moskowitz (J. Bacterial., 91, 2200–2209).

The amphipathic substance of the present invention thus obtained is soluble in both water and an oily solvent and chemically stable and therefore may be employed in the form of an oral or parenteral administration agent containing this novel substance in any desired amount, e.g., a tablet, capsule, syrup and injection, which may be prepared by conventional means of formulation.

The dosage of the amphipathic substance for administration to humans is generally 0.1–100 mg per day, preferably 1–20 mg per day, although the dosage range depends on the form in which the substance is used or administered. Within the above-described range, excellent TNF inducing effect is obtained.

BEST MODE FOR CARRYING OUT THE INVENTION:

The present invention will be described hereinunder in more detail by way of examples.

EXAMPLE 1

*Mycobacterium tuberculosis* H37Rv was cultured in Sauton medium for 8 weeks, and the cultured cells were treated with an ethanol/ether (1:1, v/v) solution. Then, a cell envelope fraction was separated from the cells which had been mechanically destroyed, and the fraction, as a starting material, was suspended in a phenol/water (1:1, v/v) solution and extracted with stirring for 1-2 hours at room temperature. The suspension was centrifuged for 45 minutes at $7,000 \times g$, an the aqueous layer was separated. Water in an amount equal to the separated aqueous layer was added to the phenol layer, and this was stirred again for 1-2 hours at room temperature. The same extraction operation was carried out one more time. The aqueous layers from the three extraction operations were collected and thoroughly dialyzed against water, then concentrated under vacuum and freeze-dried to obtain an amphipathic substance. The yield was 3.6% of the starting material. The chemical composition of the obtained substance was as follows:

|  |  |
| --- | --- |
| hexose | 40 |
| pentose | 16.8 |
| fatty acid | 15.2 |
| amino acid | 16.2 |
| amino sugar | 0.33 |
| glycerol | not detected |
| organic phosphorus | (34) |

(In this chemical composition, each of the numerical values for hexose, pentose, fatty acid, amino acid and amino sugar represents the content (mg) of each component in 100 mg of the amphipathic substance, while the numerical value for organic phosphorus represents its content (μmole) in 100 mg of the amphipathic substance. The same applies to Table I shown later.)

EXAMPLE 2

*Nocardia rubra* M-1, *Rhodococcus terrae* 70012 and *Gordona aurantiaca* 80005 were cultured under shaking in a liquid medium (pH 7.0-7.2) containing 0.5% peptone, 1% of glucose and 0.2% yeast extract for about 1 week at 30° C. Each of the three different kinds of bacteria thus obtained was extracted with a chloroform/methanol (2:1, v/v) solution and, with the residue employed as a starting material, an extraction operation was carried out by the phenol/water method similar to that employed in Example 1 to obtain an amphipathic substance derived from each kind of bacteria. The yield was 1-2% of the starting material. Table 1 below shows the chemical composition of the amphipathic substance obtained from each bacterium.

TABLE 1

| | Chemical composition of amphipathic substance (mg/100 mg) | | | | | | |
| --- | --- | --- | --- | --- | --- | --- | --- |
| Bacteria | hexose | pentose | fatty acid | amino acid | amino sugar | glycerol | organic phosphorus |
| *N. rubra* | 51 | 16.2 | 3.2 | 7.9 | 0.10 | not detected | (167)* |
| *G. aurantiaca* | 29 | 17.0 | 7.7 | 12.2 | 2.66 | " | (100) |
| *R. terrae* | 47 | 11.8 | 15.3 | 8.0 | 1.79 | " | (72) |

*Organic phosphorus: μmole/100 mg

The amphipathic substance according to the present invention has excellent TNF inducing activity as shown in Experimental Examples described below. Although in Experimental Examples, *Propionibacterium aenes* (hereinafter referred to as "P.a") attenuated by formalin was employed for priming of mice, similar TNF inducing activity is also found in the case where mice are primed by inoculation with live BCG. Further, the amphipathic substance of the present invention has low toxicity (in an acute toxicity test, no mouse died even at a dosage of 100 mg/kg), and the thermogenicity and endotoxic shock inducing activity of the substance are much weaker than those of LPS.

EXPERIMENTAL EXAMPLE 1

(1) 1.5 mg of P.a attenuated by formalin was administered intraperitoneally to groups of ICR, 5-week old female mice (available from Japan Charles River Co., Ltd.), each group consisting of 8 mice, and 11 days thereafter, 200 μg of amphipathic substance obtained from *Mycobacterium tuberculosis* in Example 1 was administered into the vein of each mouse. Two hours later, whole blood samples were taken from mice, and serums were separated from the blood samples by the conventional method. Serums were similarly separated from blood samples taken from groups of mice to which P.a or the amphipathic substance alone had been administered and also from untreated mice. Each of the serums was centrifuged for 1 hour at $39,000 \times g$. Then, one third of the supernatant was removed, and the remainder was subjected to both in vitro and in vivo experiments to measure the TNF activity in the serum.

(2) L-929 cell growth inhibiting activity

L-929 cells (hereinafter referred to as "L-cells") were suspended at a density of $5 \times 10^4$ cells/ml in RPMI-1640 medium having 10% fetal calf serum (hereinafter referred to as "FCS") added hereto, and dispensed in a microplate with 96 wells, 80 μl for each well, and then cultivation was carried out for 3 hours in 5% $CO_2$ at 37° C.

Then, the supernatant obtained in (1) was diluted with an FCS-added RPMI-1640 medium to prepare a specimen, and 100 μl of this specimen was added to each well. Further, 20 μl of 1μCi$^3$H-thymidine was added thereto. Then, cultivation was continued at 37° C. in 5% $CO_2$. Forty-eight hours later, the supernatant was discarded, and the L-cells were separated from the plate by trypsin-EDTA treatment. The separated L-cells were collected by a cell harvester, and c.p.m. of the $^3$H-thymidine taken up by the cells was measured by using a liquid scintillation counter in accordance with the conventional method.

Table II shows the results of observation of the $^3$H-thymidine uptake of the L-cells.

TABLE II

| Specimens[a] | | ³H—thymidine taken up by L-cells c.p.m.[b] | Uptake inhibiting rate[c] (%) |
|---|---|---|---|
| P·a amphipathic | substance | | |
| − | − | 102681 ± 8390 | 5.4 |
| + | − | 116712 ± 3521 | −7.49 |
| − | + | 108280 ± 440 | 0.28 |
| + | + | 18343 ± 1265 | 84.1*** |
| 10% FCS-added RPMI-1640 medium | | 115449 ± 2593 | 0 |

*** $P < 0.001$

[a] The specimens were diluted with 10% FCS-added RPMI-1640 medium to a final concentration of 1/100.

[b] Shown are values each obtained by substracting background c.p.m. (235) from the mean of the values obtained from a triplicate test carried out for each specimen.

[c] The uptake inhibiting rate is represented by $$\left(1 - \frac{\text{Uptake after specimen is added (c.p.m.)}}{\text{Uptake after RPMI-1640 is added (c.p.m.)}}\right) \times 100\ (\%)$$

(3) L-cell cytotoxicity test

L-cells were suspended at a density of $1 \times 10^5$ cells/ml in RPMI-1640 medium containing 10% FCS, and dispensed in a microplate with 24 wells, 0.5 ml for each well, and then cultured at 37° C. in 5% $CO_2$. Three hours later, the supernatant obtained in (1) and diluted with 10% FCR-added RPMI-1640 medium was added to the medium in amount of 0.5 ml, and the cultivation was further continued. Forty-eight hours later, the supernatant was removed and the survival and death rates of L-cells separated from the plate by the trypsin-EDTA treatment were measured by observation them with a phase-contrast microscope. The results are shown in Table III.

TABLE III

| Specimens[a] | | Live cells/dead cells[b] ($\times 10^{-4}$ ml) | Cytotoxicity[c] (%) |
|---|---|---|---|
| P·a amphipathic | substance | | |
| − | − | 208/5 | 2.3 |
| + | − | 205/10 | 4.7 |
| − | + | 203/12 | 5.5 |
| + | + | 5/80 | 94.1 |
| 10% FCS-added RPMI-1640 medium | | 210/6 | 2.8 |

[a] The specimens were diluted with 10% FCS-added RPMI-1640 medium to a final concentration of 1/100.

[b] Shown are the mean values of the values obtained from a duplicate test carried out for each specimen.

[c] Cytotoxicity (%) is represented by $$\frac{\text{Number of dead cells}}{\text{Number of live cells + Number of dead cells}} \times 100\ (\%)$$

(4) Tumor necrosis test

Meth-A fibrosarcoma cells were intracutaneously transplanted at a density of $2 \times 10^5$ cells/mouse into groups of BALB/C 5-week old female mice (available from Japan Charles River Co., Ltd.), each group consisting of 4 mice. Seven days after the transplantation, the diameter of each tumor reached 7–8 mm. Then, 0.3 ml of the specimen obtained in (1) was administered to each mouse from the tail vein twice (at an interval of 3 hours). Twenty-four hours after the second administration, the occurrence of any tumor necrosis was evaluated and recorded in accordance with the criteria set forth by E. Carswell et al. [Proc. Natl. Acad. Sci. U.S.A., 72, 3666 (1975)]. The results are shown in Table IV.

TABLE IV

| Specimens | | Tumor necrosis[a] (Number of mice) | | | |
|---|---|---|---|---|---|
| P.a | amphipathic substance | − | + | ++ | +++ |
| − | − | 4 | 0 | 0 | 0 |
| + | − | 4 | 0 | 0 | 0 |
| − | + | 4 | 0 | 0 | 0 |
| + | + | 1 | 2 | 1 | 0 |
| 10% FCS-added RPMI-1640 medium | | 4 | 0 | 0 | 0 |

[a] Criteria for tumor necrosis = Method of E. Carswell et al.
−: no change
+: 25–50% of the tumor necrotized
++: 50–75% of the tumor necrotized
+++: 75% or more of the tumor necrotized

EXPERIMENTAL EXAMPLE 2

(1) 1.5 mg of P.a attenuated by formalin was administered intraperitoneally to groups of ICR, 5-week old female mice (available from Japan Charles River Co., Ltd.), each group consisting of 4 mice, and 11 days thereafter, 200 μg of amphipathic substance obtained from *Gordona aurantiaca* 80005 in Example 2 was administered into the vein of each mouse. Thereafter, processing similar to that mentioned in (1) in Example 1 was carried out to obtain serums for measuring TNF activity.

(2) Using the serums obtained in the above (1) L-cell growth inhibiting activity was examined in a manner similar to that shown in (2) in Experimental Example 1. The results are shown in Table V. It should be noted that each of the reference symbols (a), (b) and (c) has the same meaning as that shown in Table II in (2) of Experimental Example 1 (the same applies to Table VI in Experimental Example 3 and Table VII in Experimental Example 4, described later).

TABLE V

| Specimens[a] | | ³H—thymidine taken up by L-cells c.p.m.[b] | Uptake inhibiting rate[c] (%) |
|---|---|---|---|
| P.a | amphipathic substance | | |
| − | − | 17530 ± 1602 | 1.6 |
| + | − | 17077 ± 877 | 4.2 |
| − | + | 16542 ± 2111 | 7.2 |
| + | + | 1788 ± 14 | 90.0*** |
| 10% FCS-added RPMI-1640 medium | | 17822 ± 1071 | 0 |

*** $P < 0.001$

EXPERIMENTAL EXAMPLE 3

Serums for measuring TNF activity were obtained in the same way as that shown in (1) in Experimental Example 1 except that the amphipathic substance obtained from *Nocardia rubra* M-1 in Example 2 was employed in place of the amphipathic substance derived from *Mycobacterium tuberculosis* H37Rv obtained in Example 1. Using these serums, L-cell growth inhibiting activity was examined by the method shown in (2) in Experimental Example 1. The results are shown in Table VI.

TABLE VI

| Specimens[a] | | ³H—thymidine taken up by L-cells c.p.m.[b] | Uptake inhibiting rate[c] (%) |
|---|---|---|---|
| P.a | amphipathic substance | | |
| − | − | 17530 ± 1602 | 1.6 |
| + | − | 14616 ± 94.5 | 18.0 |
| − | + | 17198 ± 5.0 | 3.5 |
| + | + | 4063 ± 610 | 77.2*** |

TABLE VI-continued

| Specimens[a] | | ³H—thymidine taken up by L-cells c.p.m.[b] | Uptake inhibiting rate[c] (%) |
|---|---|---|---|
| P.a | amphipathic substance | | |
| 10% FCS-added RPMI-1640 medium | | 17822 ± 1071 | 0 |

***P <0.001

EXPERIMENTAL EXAMPLE 4

Serums for measuring TNF activity were obtained in the same way as that shown in (1) in Experimental Example 1 except that the amphipathic substance obtained from *Rhodococcus terrae* 70012 in Example 2 was employed. Using these serums, L-cell growth inhibiting activity was examined by the method shown in (2) in Experimental Example 1. The results are shown in Table VII.

TABLE VII

| Specimens[a] | | ³H—thymidine taken up by L-cells c.p.m.[b] | Uptake inhibiting rate[c] (%) |
|---|---|---|---|
| P.a | amphipathic substance | | |
| − | − | 35430 ± 8449 | 8.2 |
| + | − | 29730 ± 3440 | 22.9 |
| − | + | 31394 ± 3642 | 18.6 |
| + | + | 644 ± 66 | 98.3*** |
| 10% FCS-added RPMI-1640 medium | | 38579 ± 2584 | 0 |

***P <0.001

We claim:

1. An amphipathic substance having TNF inducing activity which is obtained by extraction into an aqueous phase from an acid-fast bacterium, said amphipathic substance comprising hexose as a predominant component, as well as lesser amounts of pentose, fatty acid and amino acid, said amphipathic substance having 0.3–1.7 μmoles organic phosphorus/mg total weight and said amphipathic substance being essentially free of glycerol and essentially free of hydroxy fatty acid.

2. An amphipathic substance according to claim 1 which is obtained through extraction by the phenol/water method.

3. The amphipathic substance of claim 2, wherein said acid-fast bacterium is selected from the group consisting of genus *Mycobacterium*, genus *Nocardia*, genus *Rhodococcus*, genus *Gordona*, and genus *Corneybacterium*.

4. The substance of claim 3 having the following composition:

| hexose | 0.25–0.55 |
|---|---|
| pentose | 0.10–0.17 |
| fatty acid | 0.03–0.16 |
| amino acid | 0.07–0.17 |
| amino sugar | 0.001–0.03 |
| organic phosphorus | 0.3–1.7 |
| glycerol | not detected. | wherein the numerals represent μmole/mg for organic phosphorus and mg/mg for the other components.

5. An amphipathic substance according to claim 1, wherein said acid-fast bacterium is defined by a strain selected form among genus *Mycobacterium*, genus *Nocardia*, genus *Rhodococcus*, genus *Gordona*, and genus *Corneybacterium*.

6. An amphipathic substance according to claim 1 which has the following chemical composition:

| hexose | 0.25–0.55 |
|---|---|
| pentose | 0.10–0.17 |
| fatty acid | 0.03–0.16 |
| amino acid | 0.07–0.17 |
| amino sugar | 0.001–0.03 |
| organic phosphorus | 0.3–1.7 |
| glycerol | not detected. | wherein the numerals represent μmole/mg for organic phosphorus and mg/mg for the other components.

7. The amphipathic substance of claim 6, wherein said acid-fast bacterium is selected from the group consisting of genus *Mycobacterium*, genus *Nocardia*, genus *Rhodococcus*, genus *Gordona* and genus *Corneybacterium*.

8. A composition for the induction of tumor necrosis factor comprising an effective amount of an amphipathic substance in accordance with claim 1 and a pharmaceutically acceptable carrier.

9. A substantially pure amphipathic substance having TNF inducing activity, said substance being essentially free of glycerol, hydroxy fatty acid and muramic acid, and having the following chemical composition:

| hexose | 0.25–0.55 mg/mg |
|---|---|
| pentose | 0.10–0.17 mg/mg |
| fatty acid | 0.03–0.16 mg/mg |
| amino acid | 0.07–0.17 mg/mg |
| amino sugar | <0.03 mg/mg |
| organic phosphorus | 0.3–1.7 mole/mg, | wherein the greater part of the hexose comprises mannose, the greater part of the pentose comprises arabinose, the principal components of the fatty acid comprise palmitic acid, stearic acid and tuberculostearic acid, the chief amino acids comprise glutamic acid, aspartic acid, leucine, threonine, glycine, alanine, serine and valine, and the greater part of the amino sugar comprises glucosamine.

10. A composition for the induction of tumor necrosis factor comprising an effective amount of an amphipathic substance in accordance with claim 9 and a pharmaceutically acceptable carrier.

11. A method of inducing TNF production in humans, comprising the step of:
administering 0.1 mg/day, to a human, of an amphipathic substance obtained by extraction into aqueous phase from an acid-fast bacterium selected from the group consisting of genus *Mycobacterium*, genus *Nocardia*, genus *Rhodococcus*, genus *Gordona* and genus *Corneybacterium*, said amphipathic substance comprising hexose as a predominant component, as well as lesser amounts of pentose, fatty acid and amino acid, said amphipathic substance having 0.3–1.7 μmoles organic phosphorus/mg total weight and said amphipathic substance being essentially free of glycerol and essentially free of hydroxy fatty acid.

12. The method of claim 11, wherein said amphipathic substance is obtained through extraction by the phenol/water method.

13. The method of claim 11, wherein said amphipathic substance has the following chemical composition:

| hexose | 0.25–0.55 |
|---|---|
| pentose | 0.10–0.17 |

| | -continued |
|---|---|
| fatty acid | 0.03–0.16 |
| amino acid | 0.07–0.17 |
| amino sugar | 0.001–0.03 |
| organic phosphorus | 0.3–1.7 |
| glycerol | not detected | wherein the numerals represent μmole/mg for organic phosphorus and mg/mg for the other components.

14. The method of claim 13, wherein said amphipathic substance is obtained through extraction by the phenol/water method.

15. A method of inducing TNF production in humans, comprising administering an effective amount of an amphipathic substance in accordance with claim 1.

16. A method of inducing TNF production in humans, comprising administering an effective amount of an amphipathic substance in accordance with claim 9.

* * * * *

UNITED STATES PATENT AND TRADEMARK OFFICE
CERTIFICATE OF CORRECTION

PATENT NO. : 4,900,724
DATED     : February 13, 1990
INVENTOR(S) : KATO et al.

It is certified that error appears in the above-identified patent and that said Letters Patent is hereby corrected as shown below:

On the Face of the Patent:

| | |
|---|---|
| [73] Assignees: | Delete "Sawai Pharmaceutical Co., Ltd", insert therefor -- Sawai Pharmaceutical Co., Ltd., Osaka, Japan -- |
| | Delete "both of Osaka", insert therefor -- Tokyo -- |
| Column 7, line 48 | Delete "Corneybacterium", insert therefor -- Corynebacterium -- |
| Column 7, line 66 | Delete "Corneybacterium", insert therefor -- Corynebacterium -- |
| Column 8, line 15 | Delete "Corneybacterium", insert therefor -- Corynebacterium -- |
| Column 8, line 51 | Delete "Corneybacterium", insert therefor -- Corynebacterium -- |

Signed and Sealed this

Twenty-fourth Day of December, 1991

Attest:

HARRY F. MANBECK, JR.

*Attesting Officer*   *Commissioner of Patents and Trademarks*